US00PP12355P2

(12) United States Plant Patent
Utecht

(10) Patent No.: US PP12,355 P2
(45) Date of Patent: Jan. 15, 2002

(54) GERANIUM PLANT NAMED 'FISRIMBA'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/773,020

(22) Filed: Jan. 31, 2001

(51) Int. Cl.[7] ..... A01H 5/00
(52) U.S. Cl. ..... Plt./332
(58) Field of Search ..... Plt./332, 324

(56) References Cited

PUBLICATIONS

GTITM UPOVROM Citation For 'FISRIMBA' as per QZ PBR 991465; Oct. 20, 1999.*
Official Gazette of the Community Plant Varity Office, Dec. 15, 1999, European Community Application.
German Application and Denomination, Dec. 15, 1998.
Fischer—Schmüllung Plant Alliance Catalogue, featuring 'Fisimba' on p. 25, Germany, 2001.
Canadian application, denomination, Plant Varieties Journal No. 38, Jan. 2001, Canada. pp. 63–64.

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisrimba', as described and illustrated, and particularly characterized by the combined features of the brilliant deep-pink to cherry red flower color, large, double flowers, medium green foliage with weak zonation and glossy surface, with vigorous growth, and relatively well-branched, moderately long, trailing plant habit.

1 Drawing Sheet

BACKGROUND OF THE INVENTION

The present invention comprises a new and distinct cultivar of geranium, botanically known as *Pelargonium peltatum*, and hereinafter referred to by the cultivar name 'Fisrimba'.

'Fisrimba' is a product of a planned breeding program which had the objective of creating new geranium cultivars with pink to dark pink flower color, moderately vigorous growth, and bushy and well-branched plant habit 'Fisrimba' originated from a hybridization made by the inventor Angelika Utecht in a controlled breeding program in Galdar, Gran Canaria, Spain, in 1996.

The female parent was a hybrid seedling, no. 1793-13 (unpatented), characterized by red, single-type flowers, medium green foliage with weak zonation, and medium growth habit. The male parent of 'Fisrimba' was 'Fisberno', U.S. plant Pat. No. 10,367, having light salmon-red, double flowers, slightly zoned foliage, and very well branched plant habit.

'Fisrimba' was selected as one flowering plant within the progeny of the stated cross by Angelika Utecht in 1997 in a controlled environment in Galdar, Gran Canaria, Spain. The first act of asexual reproduction of 'Fisrimba' was accomplished when vegetative cuttings were taken from the initial selection in the fall of 1997 in a controlled environment in Galdar, Gran Canaria, Spain, by, or under the supervision of, Angelika Utecht.

Horticultural examination of plants grown from cuttings of this clone initiated in May 1998 in Hillscheid, Germany, and continuing thereafter, has demonstrated that the combination of characteristics as herein disclosed for 'Fisrimba' are firmly fixed and are retained through successive generations of asexual reproduction.

'Fisrimba' has not been observed under all possible environmental conditions. The phenotype may vary significantly with variations in environment such as temperature, light intensity and day length.

BRIEF DESCRIPTION OF THE INVENTION

The following observations, measurements, and comparisions describe plants grown in Hillscheid, Germany, and in Langley, British Columbia, Canada, under greenhouse conditions which approximate those generally used in commercial practice.

The following traits have been repeatedly observed and are determined to be basic characteristics of 'Fisrimba', which in combination distinguish this geranium as a new and distinct cultivar:

1. Large, intense pink to cherry red colored, double flowers;

2. Semi-spherically shaped inflorescences;

3. Medium green foliage with weak zonation;

4. Vigorous growth and well-branched, bushy plant habit; and

5. Early to medium spring flowering response.

Of the many commercial cultivars known to the present inventor, the most similar in comparision to 'Fisrimba' are the varieties 'Fislamda', U.S. Plant patent application Ser. No. 09/323,109 and 'Fismoli', disclosed in U.S. Plant Pat. No. 9,382.

In comparison to 'Fislamda' and 'Fismoli', 'Fisrimba' is intermediate in many respects: its flower color is a more intense pink than 'Fismoli', but a less bluish or purple tone than 'Fislamda'. Furthermore, 'Fisrimba' grows more vigorously than 'Fislamda', but its plant habit is bushier and rounder, not quite as long trailing as that of 'Fismoli'.

BRIEF DESCRIPTION OF THE DRAWING

The accompanying photographic drawing shows typical flower and foliage characteristics of 'Fisrimba' with colors being as true as possible with an illustration of this type. The measurements were taken in Langley, British Columbia, Canada, on Jul. 20, 2000. The plants were growing in 6 inch pots in a greenhouse, and had 15 weeks of cultivation time from the planting of rooted cuttings on Apr. 3, 2000. The plants had not been pinched.

In the following description color references are made to The Royal Horticulutral Society Colour Chart. The color values were determined indoors from plants developed in a greenhouse in May 2000 in Hillscheid, Germany.

Classification:

*Botanical.*—A hybrid of the species *Pelargonium peltatum* L'Hérit. ex Aiton.

*Commercial.*—Ivy geranium, cv. 'Fisrimba'.

Inflorescence:

*Umbel.*—Shape: Semi-spherical. Average diameter: 93 mm. Average depth: 50 mm. Peduncle length: 145 mm. Peduncle color: Medium to light green, RHS 143 B. Pedicel length: 27 mm, with spur. Pedicel color: Green, RHS 143 A, with a weak brownish stripe on one side, RHS 179 A. Number of flowers per umbel: Approximately 7 to 10. Lastingness of the umbel: Approximately 15 days at 18° C.

*Corolla.*—Average diameter: 52 mm. Form: Double. Shape: Nearly round, but not quite closed, there may be a narrow gap between upper and lower petals. Number of petals: 19 to 21. Size: Upper petals are 31–33 mm long, 21–23 mm wide; lower petals are approximately 26–28 mm long and 17–19 mm wide. Petal shape: Obovate, attenuate base, upper end is rounded, margin entire. Color (general tonality from a distance of three meters): Between deep pink and cherry red. Color of upper petals: RHS 58 B. Markings of upper petals: Two dark-red veins, RHS 46 A and a small dot, between RHS 46 A and RHS 46 B(not visible in the photograph), covered by inner petals. Color of lower petals: RHS 57 C, without markings. Color of lower surface of petals: Approximately 58 C, slightly variable. Color of sepals: Outer surface green, RHS 143 B; inner surface light green, RHS 143 C. Number of sepals: 5. Size of sepals: 13–14 mm long, 5 mm wide for the largest, upper sepal, 3 mm in width for the other sepals. Sepal shape: Linear to lanceolate, acute tip, truncate base, surface with weak pubescence, margin entire.

*Bud:* (*just prior to petals unfolding*).—Shape: Elliptical. Sepal Color: Light green, RHS 137 D. Petal Color: Deep cherry red, 57 B. Length: 21 mm. Width: 12 mm.

*Reproductive organs.*—Androecium: 3–5 fertile anthers, with white to pink filaments, yellow-orange pollen, RHS 30 A, moderate pollen production. Gynoecium: 5–6 lobed, dark-red stigma, whitish style, one pistil per flower. Fertility/Seed set: No seed set observed.

*Spring flowering response period.*—In Hillscheid, Germany, in 2000, plants had on average 1.5 flowers opened 12 weeks after planting of rooted cuttings (pinched plants).

*Outdoor flower production.*—Medium to rich flowering, the flower count in 2000, in Hillscheid, Germany, indicated about 3–4 inflorescences per plant in mid-May.

*Durability.*—Good shatter resistance, relatively good rain resistance. Lastingness of the individual bloom: Approximately 9 days at 18° C. Fragrance: None.

Plant:

*Foliage*—Form: Ivy-shaped, with slightly open base, moderately lobed, and with flossy and smooth upper surface. Shape: Apex obtuse, cordate base. Margin: Entire, apart from the lobes. Size of leaf: 80 mm wide, 45 mm long. Color of upper surface: Medium green, RHS 137 B. Color of lower surface: Lighter green, RHS 137 D. Zonation: Weak, color brown, near RHS 166 A. Petioles: 40–50 mm long, 2 mm diameter, dull green color approximately RHS 137 D.

*General appearance and form.*—Internode length: 40–50 mm. Branching pattern: 4.5 branches. Plant height: 41 cm as measured from the top of the soil (from the base of the main stem) to the tips of the branches (15 week old plants in Langley, Canada), 110–120 cm (in mid September in Hillscheid, Germany 31 weeks old).

Disease/pest resistance/susceptibility: None observed to date.

I claim:

1. A new and distinct cultivar of geranium plant named 'Fisrimba', as described and illustrated.

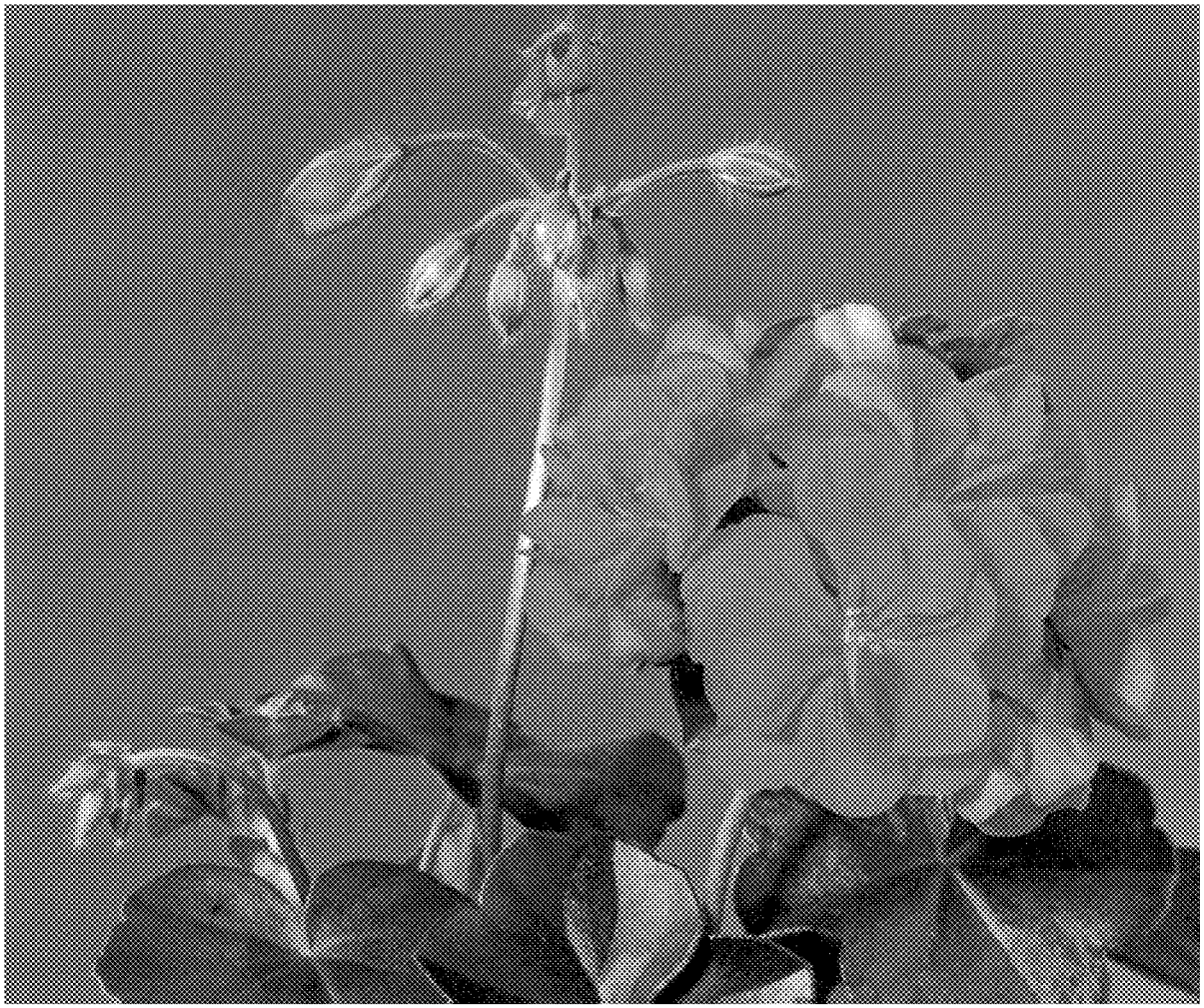

* * * * *